(12) United States Patent
Stewart et al.

(10) Patent No.: US 6,540,891 B1
(45) Date of Patent: Apr. 1, 2003

(54) TEST STRIP

(75) Inventors: Alan Andrew Stewart, Berkshire (GB); Steven Scott, Andover, MA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/674,891

(22) PCT Filed: May 6, 1999

(86) PCT No.: PCT/GB99/01424
§ 371 (c)(1),
(2), (4) Date: Jan. 11, 2001

(87) PCT Pub. No.: WO99/58709
PCT Pub. Date: Nov. 18, 1999

(30) Foreign Application Priority Data

May 8, 1998 (GB) ............................................. 9809963

(51) Int. Cl.[7] ............................................. G01N 27/327
(52) U.S. Cl. ............................. 204/403.14; 204/403.01; 204/403.15
(58) Field of Search ...................... 204/403.01, 403.06, 204/403.1, 403.11, 403.14, 403.15

(56) References Cited

U.S. PATENT DOCUMENTS 5,509,410 A * 4/1996 Hill et al. ............... 204/403.04
5,628,890 A * 5/1997 Carter et al. ........... 204/403.05

FOREIGN PATENT DOCUMENTS

| EP | 0593096 | * | 4/1994 |
| WO | 9730344 | * | 8/1997 |

OTHER PUBLICATIONS

JPO abstract of JP 09–201337 A.*

* cited by examiner

Primary Examiner—T. Tung
Assistant Examiner—Alex Noguerola
(74) Attorney, Agent, or Firm—David L. Weinstein

(57) ABSTRACT

An improved disposable test strip for use in amperometric measurement of analytes in complex liquid media, such as blood, which has three or more electrodes has been developed. This strip is designed so that different electrical potentials can be maintained between a common pseudo reference/counter electrode and each of the other electrodes upon the imposition of a common potential by an amperometric meter. This capability is imparted to the test strip by providing different circuit resistances for each of these other electrodes. The test strip can be utilized to measure a single analyte such as glucose with a background compensation via a "dummy" electrode or it can be used to measure the concentration of multiple analytes.

22 Claims, 3 Drawing Sheets

TRACK A

TRACK A

TRACK B

CONTROL

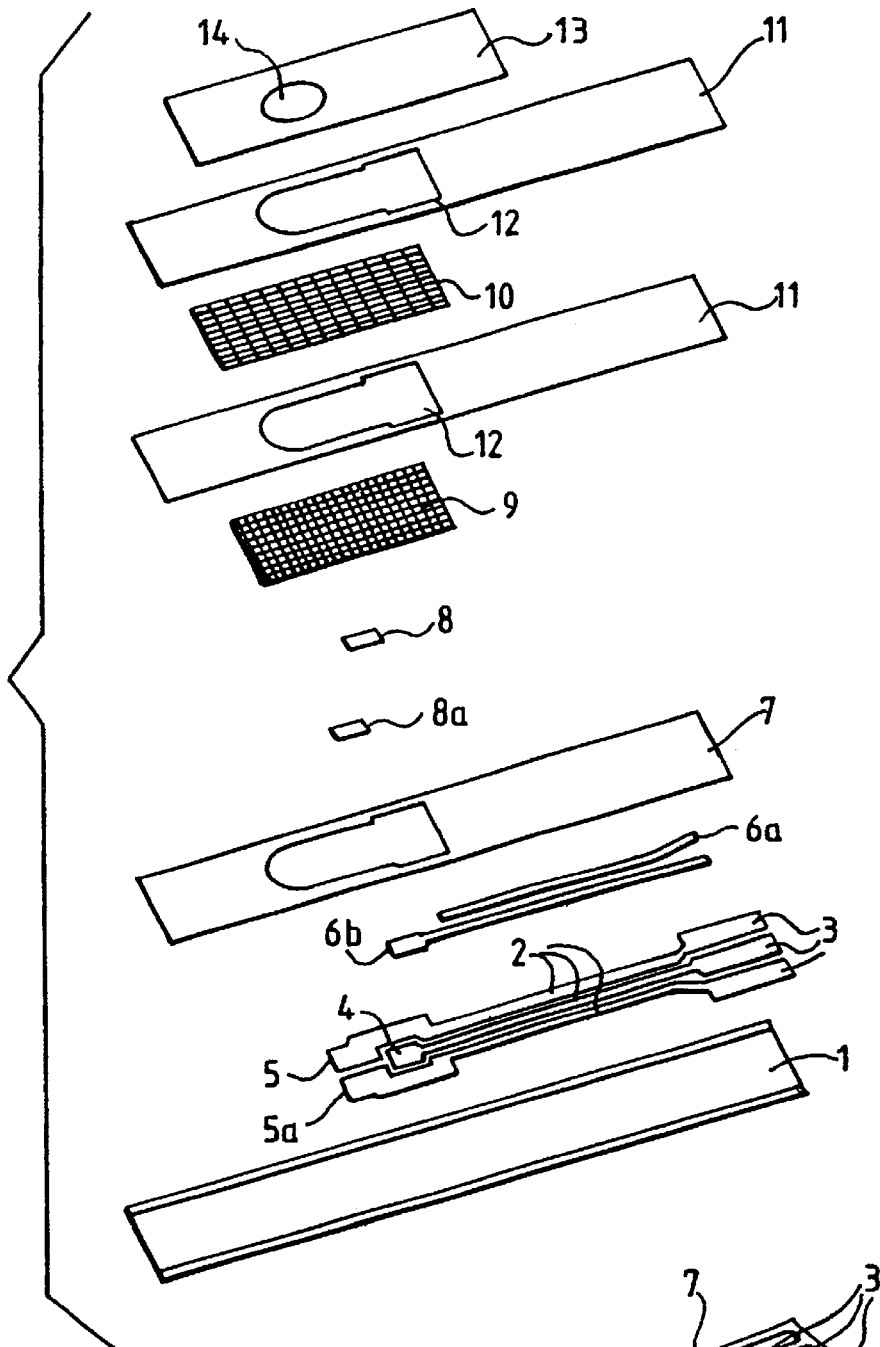
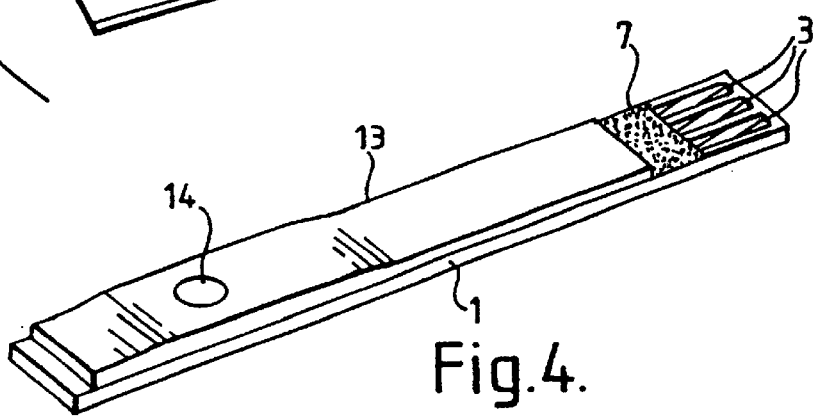

TEST STRIP

The measurement of analytes such as glucose in complex liquid media such as human blood by amperometric methods using disposable test strips has become widely used and is currently employed in a number of commercial products. In certain configurations it is advantageous to improve the signal to noise ratio by employing a three electrode system in which one electrode serves as a pseudo reference/counter electrode to establish a reference potential. Typically this is a silver/silver chloride electrode. A second, working electrode is coated with an enzyme which promotes an oxidation or a reduction reaction with the intended analyte and a mediator which transfers electrons between the enzyme and the electrode. The third "dummy" electrode is coated with the mediator but not the enzyme and it provides a measure of the current which arises from other than the oxidation reduction reaction involving the target analyte. An example of such a system is described in U.S. Pat. No. 5,628,980 to Carter, et al. (incorporated by reference herein) and is utilized in the MediSense QID glucose meter.

The three electrode system provides a good way to isolate the current which arises from the oxidation reduction reaction involving the target s analyte such as glucose but it also imposes a higher current load on the pseudo reference/counter electrode. In some testing environments such as glucose meters used by diabetics in their homes it is impractical or impossible to pretreat the samples to remove possible interferants. Thus with home use glucose meters the diabetic simply applies a sample of whole blood. Whole blood typically contains a number of electrochemically active species whose concentration may vary from person to person or even from sample to sample from the same individual. The dummy electrode provides a measure of current arising from the presence of these interferants thus allowing a normalization which removes their contribution to the current measured at the working electrode. However, in such a three electrode configuration the current seen by the pseudo reference/counter electrode includes contributions from both the working electrode and the dummy electrode. Thus in some cases the pseudo reference/counter electrode sees a significantly greater current than it would in a two electrode configuration.

The pseudo reference/counter electrode in such a configuration is, in act, serving two roles which can be inconsistent if the current it sees becomes too great. It serves, on the one hand, to provide a constant half-cell potential, i.e. a reference potential and, on the other hand, it also serves as a counter electrode balancing the electron transfer occurring at the working and dummy electrodes. For instance, in a typical glucose meter,mediator is becoming oxidized at the working and dummy electrodes so a reduction reaction needs to occur at the pseudo reference/counter electrode to balance the electron transfer. With the typical Ag/AgCl pseudo reference/counter electrode this involves the reduction of silver ions thus consuming (or reducing) silver chloride. If too much silver chloride is consumed the pseudo reference/counter electrode can no longer serve its function of providing a source of constant half-cell potential. In other words, the potential difference between the two electrode reactions such as the oxidation of a mediator at the working electrode and the reduction of silver at the pseudo reference/counter electrode will actually shift as the reaction proceeds.

One approach is to redesign the pseudo reference/counter electrode to handle higher current loads without displaying a significant shift in half-cell potential. This would normally mean increasing the size or silver concentration of the pseudo reference/counter electrode relative to the working and dummy electrodes. It is difficult to further reduce the size of the working electrode because its size has already been minimized. It is limited by the economically acceptable procedures for reproducibly manufacturing millions of such disposable test strips. On the other hand, increasing the size or silver concentration of the pseudo reference/counter electrode would significantly increase the cost of such three electrode disposable strips because silver is the most expensive material used in the construction of such strips.

Therefore, there is a need for three electrode disposable test strips for use in amperometric systems whose cost is comparable to two electrode test strips and yet have pseudo reference/counter electrodes with about the same stability as in the two electrode test strips.

It has been discovered that the current load on the pseudo reference/counter counter electrode in a disposable test strip for use in amperometric measurements with a three electrode system can be decreased and therefore its half cell potential better stabilized by increasing the resistance of the dummy electrode. This allows three electrode test strips to give better performance without changing the operating characteristics of the meters in which they are used.

Increasing the resistance of the dummy electrode not only reduces the total current passing through the pseudo reference/counter electrode but it also changes the potential at the dummy electrode's interface with the sample. Thus it is possible to have a three electrode system which can simultaneously measure the concentration of two analytes. The effective potential at the "dummy" electrode with the higher total resistance can be adjusted to be too low to effect an oxidation reduction reaction indicative of the concentration of one of the two target analytes.

It is preferred to have the resistance of the dummy electrode be at least 1000 ohms greater than that of the working electrode and it is especially preferred that the resistance differential be at least about 4000 ohms.

It is also preferred that the resistance of the dummy electrode be increased by putting a resistance in series with the active electrode surface of this electrode. Thus both the area and nature of the active surface of the dummy electrode are kept similar or identical to that of the working electrode. This can readily be achieved by increasing the resistance of the conductive track which connects the active electrode surface to the meter which applies the potential and measures the resulting current. In the typical disposable strip for amperometric analyte measurement three electrode surfaces are present on one end of an elongated flat strip and three contact pads, one for each of the electrode surfaces, are present on the other end of the strip. Each electrode surface is connected to its contact pad by a conductive track. The contact pads serve as the means to establish electrical contact between the strip and the meter which applies the potential and measures the resultant current. The conductive tracks are typically covered by an insulating layer to prevent any short circuits between them.

It is particularly preferred to increase the resistance of the conductive track of the dummy electrode by narrowing its width. If this conductive track is made of the same material as the working electrode's conductive track and has about the same thickness as the conductive track of the working electrode it will have a higher resistance. Such a mechanism of increasing resistance is particularly easy to implement in mass manufacturing.

An example of the present invention will be described in accordance with the accompanying drawings, in which:

FIGS. 1*a* and 1*b* are schematic diagrams depicting the conductive layers of electrodes of disposable test strips having dummy/second working electrodes with narrowed conductive layers;

FIG. 3 is an exploded view of a disposable test strip;

FIG. 4 is a perspective view of the assembled strip of FIG. 3; and

Figure 1A:
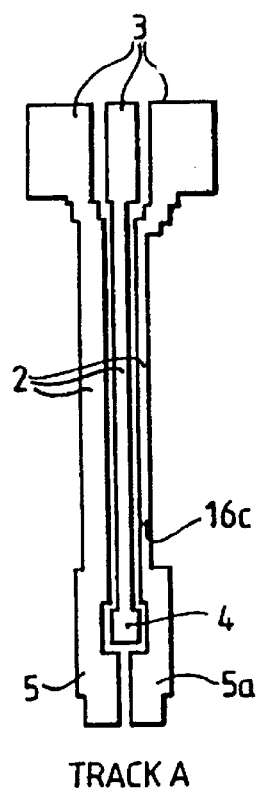

The three electrode disposable test strip for the amperometric measurement of analytes in complex liquid media is optimized to improve the signal to noise ratio without imposing an excessive current load on the reference/counter electrode by increasing the resistance of the dummy electrode, i.e. the electrode which carries the electrochemical mediator also utilized at the working electrode but which has no enzyme or other reactant selected to engage the analyte in an oxidation reduction reaction. A typical environment for the application of this concept is the three electrode test strip described in U.S. Pat. No. 5,628,890 for the determination of glucose in whole blood samples.

Such a test strip is typically constructed of an elongated strip of a rigid electrically non-conducting material such as plastic. Suitable plastics include PVC, polycarbonate or polyester. Three conductive tracks are laid on this strip so as to establish independent conductive paths from one end to the other. Each track terminates at the end adapted to be proximate to the meter used to apply electrical potential and measure the resulting currents with a contact pad that interfaces with the meter. At the distal end of the strip each track terminates in an electrode adapted to contact the complex liquid medium which carries the analyte to be measured. A typical medium is whole human blood and a typical analyte is glucose.

The working electrode is a pad which is coated with both a substance designed to engage the target analyte in an oxidation-reduction reaction and a mediator adapted to transfer electrons between the pad and the oxidation reduction reaction. A typical substance is an enzyme adapted to promote the oxidation of glucose, such as glucose oxidase, and the mediator is a compound which readily transfers electrons from the oxidation reduction reaction to the pad, such as a ferrocene derivative.

The "dummy" electrode is a pad which preferably has the same surface area as the working electrode and is coated with the same amount of the same mediator as the working electrode. The concept is to provide an environment in the immediate vicinity of this "dummy" electrode which is essentially identical to that of the working electrode except for the substance, typically an enzyme, adapted to react with the target analyte. Then the spurious electrochemical reactions which might occur at the working electrode giving rise to noise are just as likely to occur at the "dummy" electrode. Thus the signal arising from such spurious reactions can be determined by measurement at the "dummy" electrode and subtracted from the total signal measured at the working electrode. This provides an improved signal to noise ratio.

The pseudo reference/counter electrode is a pad with a material such as silver/silver chloride which has both the oxidized and reduced form of a species to provide an essentially constant half-cell potential. So long as the relative proportions of the reduced and oxidized form of this species such as silver and silver chloride are not substantially changed the half-cell potential of this electrochemical couple will remain relatively constant. This facilitates being able to maintain a known constant oxidation or reduction potential at the working electrode. This allows a production batch of disposable test strips to have a common calibration.

In the typical situation the disposable strips are utilized with a meter which functions to correlate the amount of current observed upon the application of an external potential to the contact pads of the disposable strip to the amount of analyte present. This meter is designed to assume certain electrical characteristics will be observed upon the application of this external potential. One such assumption is that the amount of current observed will decrease monotonically with time. If the current does not decay in the expected manner the meter is programmed to abort the test. If the half-cell potential of the pseudo reference/counter electrode such as a silver/silver chloride electrode shifts the current characteristics may indeed fail to meet the expectations programmed into the meter causing an aborted test.

For example the half-cell potential of the silver/silver chloride electrode will shift if the proportion of silver to silver chloride is changed. As current flows through this electrode silver is either reduced or oxidized, depending on the nature of the reaction occurring at the working electrode In the typical meter for sensing glucose concentration glucose is oxidized at the working electrode reducing the mediator. The mediator then transfers the electron or electrons it has gained in this reduction reaction to its electrode pad. These electrons are then taken up at the pseudo reference/counter electrode. In the typical case this is a silver/silver chloride electrode and the electrons are taken up by the reduction of silver ions transforming silver chloride to silver metal.

If a sufficient amount of current passes through such a pseudo reference/counter electrode the proportion of silver to silver chloride will change enough to cause a noticeable change in the half-cell potential of this electrode. If this change becomes large enough the current at the working electrode may no longer decay monotonically. This in turn will cause the meter to sense an error condition and abort the test.

The current at the working electrode arises from the oxidation reduction reaction involving the target analyte and the subsequent transfer of electrons by the mediator. In the typical glucose meter glucose is oxidized by glucose oxidase and the mediator, for instance a ferrocene derivative, then transfers the electrons liberated by the oxidation of the glucose to its electrode pad. In detail the glucose oxidase becomes reduced by oxidizing the glucose in the sample which is exposed to the disposable test strip and then is reoxidized by reducing the mediator. The mediator in turn becomes reoxidized by transferring electrons through its electrode pad to the circuit with the pseudo reference/counter electrode. Normally the current arising from this transfer decays monotonically in accordance with the Cottrell equation as the mediator in reasonable diffusion distance to the electrode pad which was reduced by reaction with glucose oxidase is reoxidized. However, this behavior is dependent upon the potential at the working electrode being held at or above a certain potential relative to the pseudo reference/counter electrode. If the potential at this pseudo reference/counter electrode shifts, the behavior at the working electrode may no longer follow this pattern.

The disposable strips are typically designed so that the pseudo reference/counter electrode does not undergo such a potential shift. For instance this electrode can be made large enough that the current generated by the analyte concentrations typically encountered does not consume enough silver ions to cause such a shift.

The use of a third, "dummy" electrode, however, imposes an additional current load on the pseudo reference/counter electrode. In the typical glucose meter where an oxidation reaction occurs at the working electrode, the reduction reaction occurring at the pseudo reference/counter electrode must balance not only the oxidation reaction at the working electrode but also any oxidation reaction occurring at the "dummy" electrode. This additional burden may be sufficient to shift the half-cell potential of the pseudo reference/counter electrode out of its design range.

This is a particular problem in glucose meters which utilize an initially reduced mediator such as a ferrocene derivative. In such a meter there is an initial high current load as the mediator is oxidized at both the working and "dummy" electrodes. If there is also a high level of glucose in the sample being tested, there will also be a fairly high current load from the reoxidation of mediator initially reduced as a result of the oxidation of the glucose. The combined current load has a tendency to adversely effect the half-cell potential of the pseudo reference/counter electrode.

The total current load on the pseudo reference/counter electrode can be reduced by increasing the resistance in the overall circuit. However, it is impractical to change the resistance in the circuit involving the working electrode. The meters used with the disposable test strips of present concern are calibrated to correlate the level of current in the working electrode circuit after sometime period or over some fixed time interval after exposure of the test strip to the sample to the concentration of target analyte. Then the meters are distributed to a large number of users who expect to use the meters with the disposable test strips for a number of years. Thus it is impractical to make any change in such test strips which would require a corresponding change in the meter with which they are used.

It has, however, been found that the resistance in the "dummy" electrode circuit can be increased without adversely effecting the interaction between the disposable test strip and its meter. The function of the "dummy" electrode is to allow subtraction from the total signal or current at the working electrode of that portion attributable to superious oxidation-reduction reactions with species in the complex liquid medium other than the target analyte. This subtraction is only of concern at the time or over the interval during which the current at the working electrode is measured for correlation to the analyte concentration. Typically such measurements are made after the resistance of the overall system is comparatively high after most of the oxidation at the working electrode has already occurred. It has been discovered that at this point the difference in electrochemical environments at the working and "dummy" electrodes is insufficient to adversely effect the function of the dummy electrode.

The relative difference in electrochemical environment between the working electrode and a "dummy" electrode with added resistance does tend to decrease as a test cycle proceeds. As the mediator subject to reoxidation at the working electrode decreases the effective resistance in the working electrode circuit increases, i.e. there are few species to support electron transfer. Thus although there will always be a fixed difference in resistance between the working and "dummy" electrodes circuits the percentage difference will decrease as the effective resistance in the working electrode circuit increases.

In an alternative embodiment, the three electrode arrangement is used to simultaneously measure the concentration of two analytes. In this case there are two working electrodes and one pseudo reference/counter electrode. The first working electrode is designed to operate with a first substance that engages one of the target analytes in an oxidation reduction reaction at a relatively low potential. The second working electrode is designed to operate with a second substance that engages the other target analyte in an oxidation reduction reaction only at a higher potential. For ease in manufacturing both working electrodes are typically coated with is both substances and appropriate mediators. However, the test strip is designed so that the second substance which is coated on the first working electrode remains inactive. In particular, the electrical resistance in the circuit path from the contact pad connected to the first working electrode through the first working electrode is significantly greatly than the electrical resistance in the circuit path from the contact pad connected to the second working electrode through the working electrode. Thus when a certain electrical potential is applied to the contact pads of both electrodes relative to the pseudo reference/counter electrode, the effective potential at the first working electrode is less than that at the second working electrode, some of the potential drop having been expended traversing the higher circuit resistance.

The two analyte embodiment is applied to the simultaneous measurement of ketones and glucose by utilizing an enzyme mediator system for the ketones which operates at +200 mV and an enzyme mediator system for the glucose which operates at +400 mv. In particular, hydroxy butyrate dehydrogenase (HBDH) with a nicotinamide adenine dinucleotide (NADH) cofactor and a 1,10-phenanthroline quinone (1,10 PQ) mediator is used for the ketones and glucose oxidase with a ferrocene derivative mediator is used for the glucose.

The low operating potential of the HBDH/NADH/1, 10 PQ system is a significant advantage for an analyte like ketones which has a limited linear response range. In the case of ketones a linear response is typically expected only over a range of between about 0 and 8 milli Molar. By operating at a low potential interference from other species which might undergo an oxidation reduction reaction at a higher potential is avoided. In other words, the probability that another chemical species in the sample might become oxidized and deliver electrons to the first working electrode thus making a superious contribution to the current sensed at this electrode is minimized.

The potential at the first working electrode is adjusted so that upon the application of a 400 mV potential between the second working electrode and the reference/counter electrode the potential between this first working electrode and the reference/counter electrode is 200 mV. This adjustment is effected by increasing the resistance of the circuit path involving this electrode relative to that involving the second working electrode by an appropriate amount in one of the ways discussed hereinabove.

The current sensed at the first working electrode is the result of the oxidation of ketones while that sensed at the second working electrode is the result of the oxidation of both ketones and glucose. The amount of current at each electrode can then be employed in a simple simultaneous equation to determine the concentration of ketones and glucose in the same sample.

It is, of course, possible to coat only the first working electrode with the ketones sensitive chemistry and to coat only the second working electrode with only the glucose sensitive chemistry. This would be expected to result in higher manufacturing costs. Typically the disposable test strips are manufactured by a series of printing steps so that applying different chemistries to each working electrode would require additional printing steps.

A particular application of the concept of a high resistance dummy electrode to the measurement of glucose is illustrated in FIGS. 1 through 5. In the strips illustrated, the working electrode and the dummy electrode each had a surface area of 6.612 square millimeters while the pseudo reference/counter electrode had a surface area of 4.18 square millimeters. The conductive tracks which connect the contact pads to the electrode pads are in most cases 0.801 millimeters. In two cases the conductive track associated with the dummy electrode was narrowed to 0.510 millimeters and 0.305 millimeters, as illustrated in FIGS. 1a and 1b.

Figure 1B:
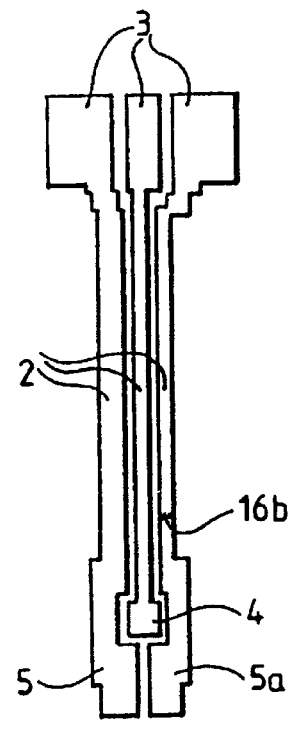
Figure 2:
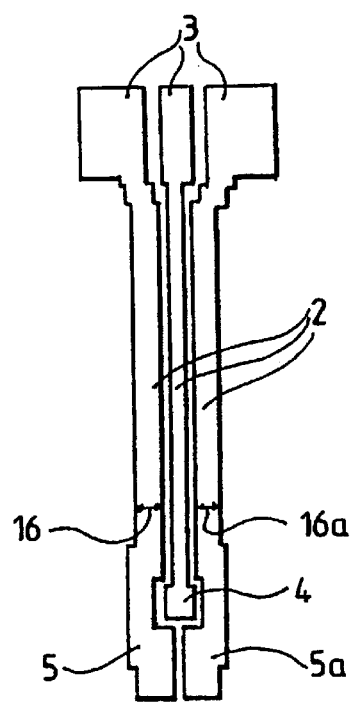
FIG. 2 is a schematic diagram depicting the conductive layers of electrodes of a control disposable test strip.

Two different conductive layer prints are illustrated in FIGS. 1a (Track A) and 1b (Track B). A control conductive layer print, in which the working and dummy electrodes have the same resistance, is shown in FIG. 2. Referring to FIGS. 1a, 1b and 2, the electrode configuration on the sensor strips has three printed layers of electrically conducting carbon ink 2. The layers define the positions of the pseudo reference/counter electrode 4, the working electrode 5, the dummy electrode 5a and electrical contacts 3.

Referring to FIG. 2, working electrode 5 has a track width 16 that is equal to track width 16a of dummy electrode 5a. Equal track widths 16 and 16a give the working electrode and dummy electrode equal resistances. Referring to FIGS. 1a and 1b, track widths 16b and 16c of dummy electrode 5a are narrower than track width 16a of the control in FIG. 2. The conductive layer of dummy electrode 5a is narrowed in order to increase the resistance of the dummy electrode relative to the working electrode resistance. Track width 16c is smaller than track width 16b. Thus, the resistance of dummy electrode 5a in Track A (FIG. 1a) is greater than the resistance of dummy electrode 5a in Track B (FIG. 1b).

The composition of the conductive layers can also affect the resistance of the electrodes. Generally, the conductive layers of the electrodes are printed at the same time with the same ink. The conductive layers can be printed with a low carbon-content ink or a high carbon-content ink. Low carbon-content had a carbon content of between 30 and 31 weight percent and a resin content of between 7 and 9 weight percent. The high carbon-content ink has a carbon content of between 42 and 45 weight percent, and a resin content of between 7 and 9 weight percent.

A suitable electrode sensor strip is illustrated in FIGS. 3 and 4. Referring to FIGS. 3 and 4, the electrode support 1, an elongated strip of plastic material (e.g., PVC, polycarbonate, or polyester) supports three printed tracks of electrically conducting carbon ink 2. These printed tracks define the positions of the pseudo reference/counter electrode 4, of the working electrode 5, of the dummy electrode 5a, and of the electrical contacts 3 that are inserted into an appropriate measurement device (not shown). The conductive layer of dummy electrode 5a is narrowed in order to increase the resistance of the dummy electrode relative to the working electrode.

The elongated portions of the conductive tracks are each overlaid with silver/silver chloride particle tracks 6a and 6b, with the enlarged exposed area overlying 4, and 6b and 4 together forming the pseudo reference/counter electrode. The conductive track or layer for dummy electrode 5a is not overlaid with silver/silver chloride. This further increases the resistance of the dummy electrode. The conductive tracks are further overlaid with a layer of hydrophobic electrically insulating material 7 that leaves exposed only the positions of the pseudo reference/counter electrode, the working electrode and the dummy electrode, and the contact areas. This hydrophobic insulating material prevents short circuits. Because this insulating material is hydrophobic, it can confine the sample to the exposed electrodes. A preferred insulating material is available as POLYPLAST□ (Sericol Ltd., Broadstairs, Kent, UK).

The working electrode working area 8 is formed from an ink that includes a mixture of an enzyme, a mediator, and a conductive material. The dummy electrode working area is formed from ink that includes a mixture of a mediator and a conductive material without enzyme. The respective inks are applied to the positions 5 and 5a of carbon tracks 2 as discrete areas of fixed length. Alternatively, instead of an enzyme, electrode layer 8 can contain a substrate catalytically reactive with an enzyme to be assayed. The conductive material in a preferred embodiment includes particulate carbon having the redox mediator adsorbed thereon.

A printing ink is formed as an aqueous solution of the conductor and adsorbed redox mediator. For the working electrode, it also includes the enzyme or, alternatively, a substrate. When the analyte to be measured is blood glucose, the enzyme is preferably glucose oxidase, and the redox mediator is a ferrocene derivative.

The ink can be screen printed. The ink can include a polysaccharide (e.g., a guar gum or an alginate), a hydrolyzed gelatin, an enzyme stabilizer (e.g., glutamate or trehalose), a film-forming polymer (e.g., a polyvinyl alcohol), a conductive filler (e.g., carbon), a redox mediator (e.g., ferrocene or a ferrocene derivative), a defoaming agent, a buffer, and an enzyme or a substrate. The ink printed on a dummy electrode lacks the enzyme or the substrate.

The pseudo reference/counter electrode 6b is situated relative to the working electrode 8 and dummy electrode 8a such that it is in a non-ideal position for efficient electrochemical function. The electrodes are arranged not to minimize the effect of the resistance of the solution on the overall resistance of the circuit (as is conventional). Positioning the pseudo reference/counter electrode downstream of the working electrode has the advantage of preventing completion of a circuit (and thus detection of a response) before the working electrode has been completely covered by sample.

The electrode area is overlaid by a fine grade mesh 9. This mesh protects the printed components from physical damage. It also helps the sample to wet the pseudo reference/counter electrode and working electrode by reducing the surface tension of the sample, thereby allowing it to spread evenly over the electrodes. Preferably, this mesh layer extends over the whole length of the sample path, between and including, the application point and the electrode area. Preferably, this mesh is constructed of finely woven nylon strands. Alternatively, any woven or nonwoven material can be used, provided it does not occlude the surface of the electrode such that normal diffusion is obstructed. The thickness of the mesh is selected so that the resulting sample depth is sufficiently small to produce a high solution resistance. Preferably, the fabric is not more than 70 $\mu$m in thickness. Preferably the mesh has a percent open area of about 40 to about 45%, a mesh count of about 95 to about 115 per cm, a fiber diameter of about 20 to about 40 $\mu$m, and a thickness of from about 40 to about 60 $\mu$m. A suitable mesh is NY64 HC mesh, available from Sefar (formerly ZBF), CH-8803, Ruschlikon, Switzerland.

The mesh can be surfactant coated. This is only necessary if the mesh material itself is hydrophobic (for example, nylon or polyester). If a hydrophilic mesh is used, the surfactant coating can be omitted. Any suitable surfactant can be used to coat the mesh, so long as it allows adequate even spreading of the sample. A preferred surfactant is FC 170C FLUORAD□ fluorochemical surfactant (3M, St. Paul, Minn.). FLUORAD™ is a solution of a fluoroaliphatic oxyethylene adduct, lower polyethylene glycols, 1,4-dioxane, and water. A preferred surfactant loading for most applications is from about 15–20 μg/mg of mesh. The preferred surfactant loading will vary depending on the type of mesh and surfactant used and the sample to be analyzed. It can be determined empirically by observing flow of the sample through the mesh with different levels of surfactant.

A second layer of coarser surfactant coated mesh 10 is applied over the first mesh. This second mesh layer controls the influx of the sample as it travels from the application point toward the pseudo reference/counter and working electrode areas by providing a space into which the displaced air within the sample transfer path can move as the sample moves preferentially along the lower fine grade mesh layer 9 and partially in mesh layer 10. The spacing of the larger fibers of the secondary mesh layer, perpendicular to the direction of sample flow, helps to control the sample flow by presenting repeated physical barriers to the movement of the sample as it travels through the transfer path. The regular pattern of the mesh fibers ensures that the sample progresses in stages and that only samples with sufficient volume to generate an accurate response are able to pass all the way along the pathway and reach the pseudo reference/counter electrode.

Preferably, mesh 10 is of a woven construction, so that it presents a regular repeating pattern of mesh fibers both perpendicular to and parallel to the longest aspect of the strip. Generally, the second mesh layer should be substantially thicker than the first mesh, with larger diameter mesh fibers and larger apertures between them. The larger mesh preferably has a thickness of from 100 to 1000 μm, with a thickness of from 100 to 150 μm being most preferred. A preferred mesh has a percent open area of about 50 to about 55%, a mesh count of from about 45 to about 55 per cm, and a fiber diameter of from about 55 to about 65 μm. A preferred mesh is NY151 HC mesh, also available from Sefar, CH-8803, Rushchlikon, Switzerland.

Mesh 10 is also provided with a coating of a suitable surfactant (unless the mesh itself is hydrophilic). Preferably, it is the same surfactant as that on the first mesh layer. The loading of surfactant is lower on mesh 10 than on mesh 9, providing a further barrier to movement of sample past the transverse fibers of mesh 10. In general, a loading of 1–10 μg/mg of mesh is preferred.

The mesh layers 9 and 10 are held in place by layers of hydrophobic electrically insulating ink 11. These layers can be applied by screen printing the ink over a portion of the peripheries of the meshes. Together, the layers and mesh surround and define a suitable sample transfer path 12 for the sample to travel from the application point at the furthest end of the strip towards the working electrode and pseudo reference/counter electrode. The ink impregnates the mesh outside of path 12. The insulating material thus defines sample transfer path 12 by not allowing sample to infiltrate the area of mesh covered by the layers of insulating material. A preferred insulating ink for impregnating the mesh layers is SERICARD™ (Sericol, Ltd., Broadstairs, Kent, UK).

The upper part of the electrode is enclosed by a liquid/vapor impermeable cover membrane 13. This can be a flexible tape made of polyester or similar material which includes a small aperture 14 to allow access of the applied sample to the underlying surfactant coated mesh layers. The impermeable cover membrane encloses the exposed working electrode and pseudo reference/counter electrode. Thus, it maintains the available sample space over the electrodes at a fixed height which is equivalent to the thickness of both mesh layers 9 and 10. This ensures that the solution resistance is kept at a high level. Any sample thickness up to the maximum depth of the two mesh layers is adequate in this respect. Aperture 14 is positioned overlying the furthest end of the open mesh area, remote from the pseudo reference/counter electrode 6b, such that the exposed area of mesh beneath the aperture can be used as a point of access or application for the liquid sample to be measured. The aperture can be of any suitable size large enough to allow sufficient volume of sample to pass through to the mesh layers. It should not be so large as to expose any of the area of the electrodes. The aperture is formed in the cover membrane by any suitable method (e.g., die punching). The cover membrane is affixed to the strip along a specific section, not including the electrodes, the sample transfer path or application area, using a suitable method of adhesion. Preferably this is achieved by coating the underside of a polyester tape with a layer of hot melt glue which is then heat welded to the electrode surface. The hot melt glue layer is typically of a coating weight between 10–50 $g/m^2$, preferably from 20 to 30 $g/m^2$. Pressure sensitive glues or other equivalent methods of adhesion may also be used. Care should be taken when the tape is applied, the heat and pressure applied to the cover membrane can melt the SERICARD™ and can cause it to smear onto adjoining areas.

The upper surface of the cover membrane can also be usefully provided with a layer of silicone or other hydrophobic coating which helps to drive the applied sample onto the portion of exposed surfactant coated mesh at the application point and thus make the application of small volumes of sample much simpler.

In use, a disposable test strip of the invention is connected, via electrode contacts 3, to a meter (not shown). A sample is applied to aperture 14, and moves along the sample transfer path 12. The progress of the sample is sufficiently impeded by mesh layer 10 to allow the sample to form a uniform front rather than flowing non-uniformly. Air is displaced thorough the upper portion of mesh layer 10 to and through aperture 14. The sample first covers working electrode 5 in its entirety, and only then approaches and covers pseudo reference/counter electrode 4. This completes the circuit and causes a response to be detected by the measuring device.

The effect of increasing the resistance of a dummy electrode in a system for measuring glucose in a whole blood sample was electronically modeled. In particular, Medisense G2a disposable test strips which utilize glucose oxidase and a ferrocene mediator were tested using venous blood spiked with glucose to a concentration of 15 mM. The electronics was used to simulate the effect of having a dummy electrode with each of five added resistances from zero to infinity (no dummy electrode). An initial potential relative to the pseudo reference/counter electrode of 400 mV was imposed on the working electrode and the current at the working electrode was monitored over time. The results were reported in FIG. 5.

Figure 5:
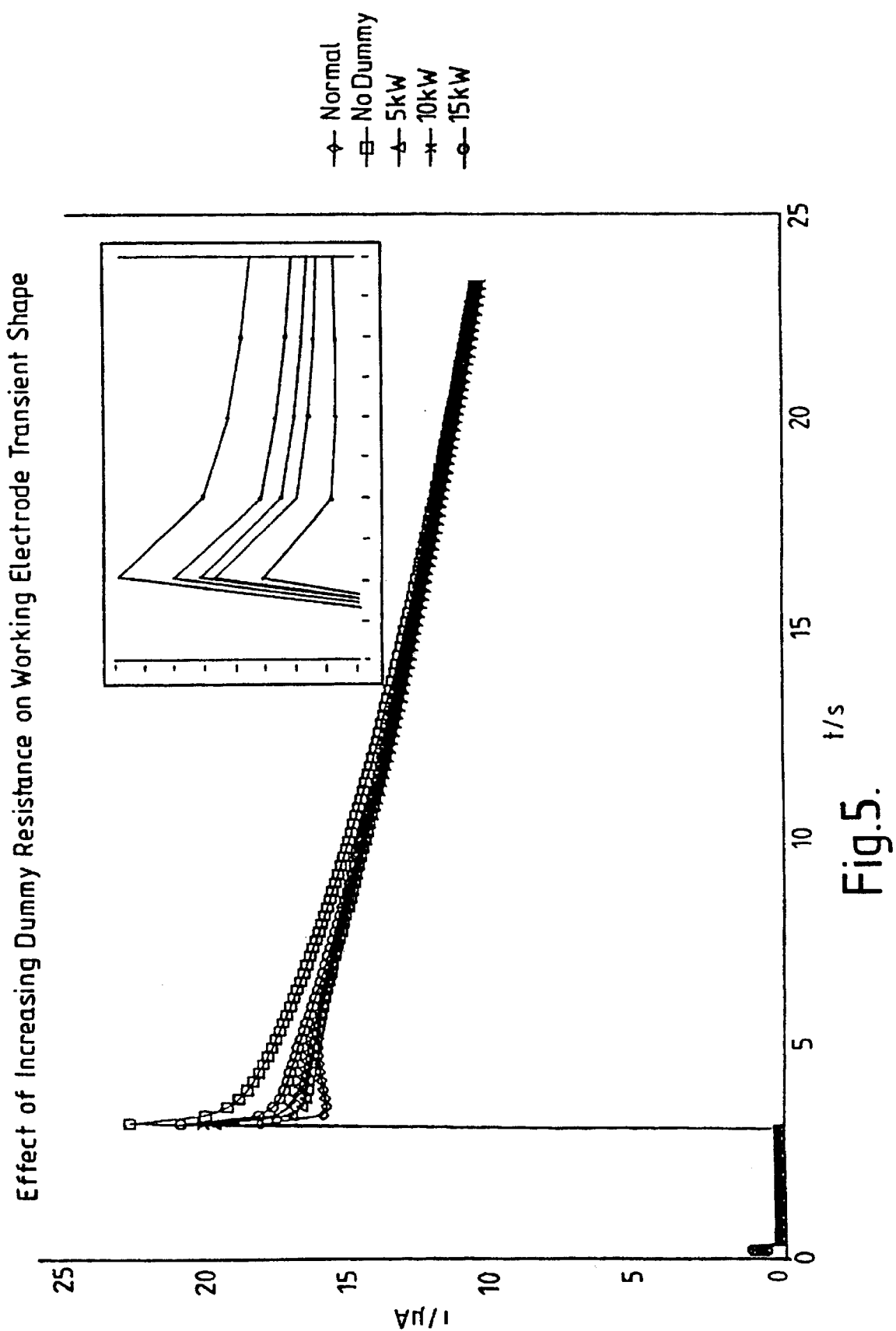
FIG. 5 is a series of plots of current in microamps versus time in seconds for a working electrode subjected to an initial potential of 400 milliVolts in the presence of a glucose containing sample for various dummy electrode configurations.

FIG. 5 illustrates that as the resistance increases so does the current at the working electrode. This is an indirect indication that the half cell potential of the pseudo reference/counter electrode is being stabilized. In an ideal situation the current at the working electrode should be independent of the resistance of the dummy electrode and should just depend upon the rate at which glucose is oxidized. However, in the real world the extra current load imposed on the pseudo reference/counter electrode by the dummy electrode does cause an observable shift in the half cell potential of the pseudo reference/counter electrode. This in turn has an effect upon the current observed at the working electrode. As the potential difference between the working and pseudo reference/counter electrodes decreases because of this shift so does the current at the working electrode.

In addition, under some conditions the current decay at the working electrode departs from the expected model. In particular, it is expected the current will decrease monotonicly with time and tend to exhibit the behavior predicted by the Cottrell equation. However, under certain conditions when the dummy electrode is imposing a significant current load on the pseudo reference/counter electrode the current at the working electrode departs from classical behavior and may actually increase with time over some short time period. This is clearly illustrated in the lowest most curve of FIG. 5, which represents a disposable test strip in which there is no resistance differential between the circuit path involving the working electrode and that involving the dummy electrode.

The glucose meters with which the disposable test strips of present concern are typically used have electronic features designed to detect invalid test results. One of these check features is a monitoring of the current decay at the working electrode. If this decay is not monotonic the meter will report an error condition and abort the test.

Thus increasing the resistance of the dummy electrode has been shown to be effective in decreasing the likelihood of a non-monotonic current decay at the working electrode and the consequent abortion of a test.

We claim:

1. A disposable test strip suitable for attachment to the signal readout circuitry of a meter which performs an amperometric test to detect a current representative of the concentration of an analyte in a complex liquid medium comprising:
   (a) a working electrode which comprises an electrode pad coated with both a substance designed to engage said analyte in an oxidation-reduction reaction and a mediator compound which will transfer electrons between the oxidation-reduction reaction and the electrode pad;
   (b) a dummy electrode which comprises an electrode pad which is coated with about the same amount of mediator compound as the working electrode but lacks the substance which engages the analyte in the oxidation-reduction reaction;
   (c) a pseudo reference/counter electrode which comprises an electrode pad coated with a material which contains both the oxidized and reduced form of a chemical species which is designed to undergo a reduction or oxidation reaction to balance the opposite reaction at the working and dummy electrodes; and
   (d) three conductive tracks, each of which extends from a contact pad adapted to interface with said readout circuitry to one of the electrode pads and which is in electrical contact with both its contact pad and its electrode pad;
wherein the electrical resistance in the circuit path from the contact pad connected to the dummy electrode through the dummy electrode is significantly greater than the electrical resistance in the circuit path from the contact pad connected to the working electrode through the working electrode.

2. The disposable test strip of claim 1 wherein the greater electrical resistance in the dummy electrode circuit is provided by increasing the resistance of the conductive track connecting the dummy electrode to its contact pad.

3. The disposable test strip of claim 1, further comprising an elongate support having a substantially flat, planar surface arranged to be releasably attached to the readout circuitry.

4. The disposable test strip of claim 3 wherein the three conductive tracks are created by coating conductive particles on the elongated support.

5. The disposable test strip of claim 4 wherein the conductive particles comprise carbon.

6. The disposable test strip of claim 4 wherein a greater electrical resistance is imparted to the conductive track connecting the dummy electrode to its contact pad by using a smaller volume of conductive particles in this track as compared to that used in the conductive track connecting the working electrode to its contact pad.

7. The disposable test strip of claim 1 wherein the conductive track connecting the dummy electrode to its contact pad is narrower than the conductive track connecting the working electrode to its contact pad.

8. The disposable test strip of claim 1 wherein the conductive track connecting the dummy electrode to its contact pad is thinner than the conductive track connecting the working electrode to its contact pad.

9. The disposable test strip of claim 1 wherein the conductive track connecting the dummy electrode to its contact pad has a different composition than the conductive track connecting the working electrode to its contact pad.

10. The disposable test strip of claim 9 wherein both the conductive track connected to the dummy electrode and the conductive track connected to the working electrode are comprised of carbon particles but only the latter conductive track is coated with silver.

11. The disposable test strip of claim 1 wherein the conductive track connecting the dummy electrode to its contact pad is longer than the conductive track connecting the working electrode to its contact pad.

12. The disposable test strip of claim 1 wherein the analyte is glucose and the substance engaging the analyte in an oxidation reduction reaction is an enzyme.

13. The disposable test strip of claim 12 wherein the enzyme is glucose oxidase.

14. The disposable test strip of claim 1 wherein the mediator is a ferrocene derivative.

15. The disposable test strip of claim 1 wherein said pseudo reference/counter electrode comprises an electrode pad coated with a mixture of silver and silver chloride.

16. The disposable test strip of claim 1 wherein the electrical resistance in said dummy electrode circuit is at least 1000 ohms greater than in said working electrode circuit path.

17. A disposable test strip suitable for attachment to the signal readout circuitry of a meter which performs an amperometric test to detect currents representative of the concentrations of multiple analytes in a liquid medium comprising:
   (a) a first working electrode which comprises an electrode pad coated with both a substance designed to engage one of the multiple analytes in an oxidation-reduction reaction at a first electrical potential difference and a mediator compound which will transfer electrons between its oxidation-reduction reaction and its electrode pad;
   (b) a second working electrode which comprises an electrode pad which is coated with both a substance designed to engage another of the multiple analytes in an oxidation-reduction reaction at a second electrical potential difference which is significantly greater than said first electrical potential difference and another mediator compound which will transfer electrons between its oxidation-reduction reaction and its electrode pad;

(c) a pseudo reference/counter electrode which comprises an electrode pad coated with a material which contains both the oxidized and reduced form of a chemical species which is designed to undergo a reduction or oxidation reaction to balance the opposite reactions at the first and second working electrodes; and (d) three conductive tracks, each of which extends from a contact pad intended to interface with said readout circuitry to one of the electrode pads and which is in electrical contact with both its contact pad and its electrode pad;

wherein the electrical resistance in the circuit path from the contact pad connected to the first working electrode through the first working electrode is significantly greater than the electrical resistance in the circuit path from the contact pad connected to the second working electrode through the second working electrode.

18. The disposable test strip of claim 17 wherein there are only two working electrodes.

19. The disposable test strip of claim 17 wherein the pseudo reference/counter electrode comprises an electrode pad coated with a mixture of silver and silver chloride.

20. The disposable test strip of claim 17 wherein the first working electrode comprises an enzyme system adapted to engage ketones and a suitable mediator and the second working electrode comprises an enzyme suitable to engage glucose and a suitable mediator.

21. The disposable test strip of claim 20 wherein the first working electrode comprises a HBDH/NADH/1, 10 PQ system and the second working electrode comprises a glucose oxidase and a ferrocene based mediator.

22. The disposable test strip of claim 21 wherein the resistance in the first working electrode circuit is such that when a 400 mV potential exists between the second working electrode and the pseudo reference/counter electrode there is a 200 mV potential between the first working electrode and the pseudo reference/counter electrode.

* * * * *